| United States Patent [19] | [11] Patent Number: 4,873,260 |
| Alberts et al. | [45] Date of Patent: Oct. 10, 1989 |

[54] TREATMENT OF DIABETIC KETOACIDOSIS

[75] Inventors: Alfred W. Alberts, Princeton, N.J.; Michael D. Greenspan, New York, N.Y.

[73] Assignee: Merck & Co., Inc., Rahway, N.J.

[21] Appl. No.: 212,769

[22] Filed: Jun. 27, 1988

[51] Int. Cl.$^4$ ............................................. A61K 31/335
[52] U.S. Cl. ................................... 514/449; 514/866; 514/432; 514/150
[58] Field of Search ................................. 514/449, 150

[56] References Cited

U.S. PATENT DOCUMENTS 4,806,564  2/1989  Chabala et al. ...................... 514/449

OTHER PUBLICATIONS

Adlridge et al., *J. Chem Soc.*, pp. 3888–3891.
Omura et al., *J. Antibiotics*, 40, pp. 1356–1357, (1987).
Greenspan et al., *Proc. Nat. Acid Sci U.S.A.*, 84, pp. 7488–7492, (1987).

*Primary Examiner*—Frederick E. Waddell
*Attorney, Agent, or Firm*—David L. Rose; Hesna J. Pfeiffer

[57] ABSTRACT

There is disclosed the use of β-lactone alkylene carboxylic acids and derivatives thereof, which are known compounds, for the use of treating diabetic ketoacidosis. The compounds are administered orally or parenterally and compositions containing the β-lactone alkylene carboxylic acid compounds as the active ingredient are also disclosed.

9 Claims, No Drawings

TREATMENT OF DIABETIC KETOACIDOSIS

BACKGROUND OF THE INVENTION

β-lactone alkylene carboxylic acids are known compounds which have antihypercholesterolemic activity. The preparation of such compounds is described in copending patent application Ser. Nos. 07/021848, 07/053646 and 07/053774, now U.S. Pat. Nos. 4,847,271, 4,816,477 and 4,806,564, respectively.

Diabetic ketoacidosis is a condition observed in uncontrolled diabetic patients resulting in increased production of acetoacetic acid and β-hydroxybutyric acid. While an insulin dependent (Type I) diabetic patient may also have high insulin levels the ketoacidotic state must be differentiated from insulin shock. Diabetic ketoacidosis is indicated in a diabetic patient by changes in sensorium such as confusion or coma; air hunger, rapid deep breathing in an attempt to compensate for metabolic acidosis; a fruity acetone odor on the breath; nausea and vomiting; possibly abdominal tenderness; extreme thirst and dry mucous membranes reflecting water depletion; and rapid weight loss. Diabetic ketoacidosis can be a very serious and even life threatening complication of diabetes and if not rapidly attended to can lead to death. Treatment of ketoacidosis can involve IV sodium bicarbonate which may result in saline overload in severe cases, and a too rapid rise in carbon dioxide level can result in an electrolyte imbalance, a dulling of the senses, coma or death. Thus, a more satisfactory treatment of ketoacidosis would be a most welcome addition to the armamentarium available in the successful management of a diabetic patient.

In addition to being a complication of diabetes management, ketoacidosis can also occur as a result of renal failure, the ingestion of exogenous poisons such as ethylene glycol, salicylates, methanol, paraldehyde and the like, and during a gastrointestinal alkali loss such as during severe diarrhea, and with ileostomy and colostomy therapy. Treatment is similar to that used in diabetic ketoacidosis and is somewhat simplified since the simultaneous management of diabetes is not involved, however, the treatment still suffers from the same disadvantages and possible side effects which may be severe.

The instant invention is a significant improvement in the management of a ketoacidotic emergency.

SUMMARY OF THE INVENTION

The instant invention is a novel treatment of ketoacidosis which involves the administration of a β-lactone alkylene carboxylic acid or derivative thereof to a ketoacidotic patient. Thus, it is an object of the instant invention to describe such β-lactone alkylene carboxylic acids. It is a further object of this invention to describe the preparation of such compounds. A still further object is to describe the compositions which may be administered to a ketoacidotic patient to treat such a condition. Further objects will be apparent from a reading of the following description.

DESCRIPTION OF THE INVENTION

The present invention is directed to novel compounds represented by the following general structural formula (I):

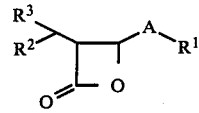

wherein:
$R^1$ is selected from
  (1) hydrogen,
  (2) hydroxy,
  (3) $C_{1-6}$ alkoxy,
  (4) phenyl,
  (5) $COR^4$
$R^4$ is
  (1) hydroxy
  (2) $C_{1-6}$ alkoxy,
  (3) substituted $C_{1-6}$ alkoxy in which the substituent is a phenyl group,
  (4) amino,
  (5) $C_{1-6}$ alkylamino,
  (6) substituted $C_{1-6}$ alkylamino in which the substituent is a hydroxy group,
  (7) phenylamino,
  (8) substituted phenyl amino in which the substituent is a halogen; and
  (9) 2-thiopyridine;
$R^2$ is
  selected from
  (1) hydrogen,
  (2) halogen,
  (3) cyano,
  (4) azido,
  (5) $C_{1-6}$ alkylcarbonylthio,
  (6) $C_{1-6}$ alkyl,
  (7) $C_{1-6}$ alkoxy,
  (8) $C_{2-6}$ alkenyloxy,
  (9) formyloxy,
  (10) $C_{1-6}$ alkylcarbonyloxy,
  (11) carboxy $C_{1-6}$ alkylcarbonyloxy,
  (12) anisyldiphenylmethyloxy,
  (13) $C_{1-6}$ alkylsulfonyloxy,
  (14) aminocarbonyloxy, and
  (15) $C_{1-6}$ alkylaminocarbonyloxy;
$R^3$ is
  selected from
  (1) hydrogen,
  (2) $C_{1-6}$ alkyl,
  (3) $C_{1-6}$ alkenyl,
  (4) phenyl, or
$R^2$ and $R^3$ when taken together with the carbon atom to which they are attached form a $C_{3-6}$ carbocyclic ring;
A is selected from
(1)

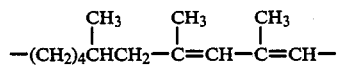

(2) $C_{6-17}$ alkylene, straight chain or branched chain,
(3) substituted $C_{6-17}$ alkylene in which the one or two substituents are
  (a) oxo,
  (b) epoxy,
  (c) geminal dihydroxy,
  (d) $C_{1-6}$ alkoxy, and
  (e) 4-bromophenylhydrazono;
(4) monounsaturated $C_{6-17}$ alkylene, and (5) substituted monounsaturated C$_{6-17}$ alkylene in which the one or two substituents are
   (a) oxo,
   (b) epoxy,
   (c) geminal dihydroxy,
   (d) C$_{1-6}$ alkoxy, and
   (e) 4-bromophenylhydrazono:
(6) C$_{7-16}$ aralkylene, wherein the alkyl chain is interupted by a 1,2-, 1,3-, or 1,4-phenylene moiety,
(7) C$_{6-18}$ alkylene, straight or branched chain, interupted by an oxygen, sulfur or sulfoxide moiety,
(8) a group of the structure

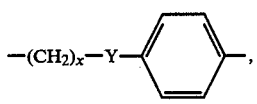

Where x is 1–4 and y is O, S or SO; the broken line indicates a single or double bond between the carbon atoms connected by such broken line; and the pharmaceutically acceptable salts thereof.

One embodiment of the compounds of the present invention is the class of compounds of the formula (I) wherein R$^2$ is hydrogen and the broken line represents a single bond connecting the carbon atoms it is situated between (hereafter a "connecting single bond"). Exemplifying this embodiment are the following compounds:
   (1) 11-(3-methyl-4-oxo-2-oxetano)-3,5,7-trimethyl-2,4-undecadienoic acid; and
   (2) methyl 11-(3-methyl-4-oxo-2-oxetano)-3,5,7-trimethyl-2,4-undecadienoate;

A second embodiment of the compounds of the present invention is the class of compounds of the formula (I) wherein R$^2$ is halogen and the broken line is a connecting single bond. A specific sub-class of this embodiment are the compounds of the formula (I) wherein R$^1$ is COR$^4$ and R$^4$ is hydroxy. Exemplifying this sub-class are the following compounds:
   (1) 11-(3-chloromethyl-4-oxo-2-oxetano)-3,5,7-trimethyl-2,4-undecadienoic acid;
   (2) 11-(3-bromomethyl-4-oxo-2-oxetano)-3,5,7-trimethyl-2,4-undecadienoic acid; and
   (3) 11-(3-fluoromethyl-4-oxo-2-oxetano)-3,5,7-trimethyl-2,4-undecadienoic acid.

A third embodiment of the compounds of the present invention is the class of compounds of the formula (I) wherein R$^2$ is cyano and the broken line is a connecting single bond. A specific sub-class of this embodiment are the compounds of the formula (I) wherein R$^1$ is COR$^4$ and R$^4$ is C$_{1-6}$ alkoxy. Exemplifying this sub class is the following compound:
   (1) methyl 11-(3 cyanomethyl-4-oxo-2-oxetano)-3,5,7-trimethyl-2,4-undecadienoate.

A fourth embodiment of the compounds of the present invention is the class of compounds of the formula (I) wherein R$^2$ is azido and the broken line is a connecting single bond. A specific sub class of this embodiment are the compounds of the formula (I) wherein R$^1$ is COR$^4$ and R$^4$ is C$_{1-6}$ alkoxy. Exemplifying this sub class is the following compound:
   (1) methyl 11-(3 azidomethyl 4-oxo-2-oxetano)-3,5,7-trimethyl-2,4-undecadienoate.

A fifth embodiment of the compounds of the present invention is the class of compounds of the formula (I) wherein R is C$_{1-6}$ alkylcarbonylthio and the broken line is a connecting single bond. A specific sub-class of this embodiment are the compounds of the formula (I) wherein R$^1$ is COR$^4$ and R$^4$ is C$_{1-6}$ alkoxy. Exemplifying this sub class is the following compound:
   (1) methyl 11-(3 acetylthiomethyl-4-oxo-2-oxetano)-3,5,7-trimethyl-2,4-undecadienoate.

Another embodiment of the compounds of the present invention is the class of compounds of the formula (I) wherein R$^2$ is hydrogen and the broken line is a connecting double bond. A specific subclass of this embodiment are the compounds of the formula (I) wherein R$^1$ is COR$^4$ and R$^4$ is hydroxy or C$_{1-6}$ alkoxy. Exemplifying this sub-class is the following compound:
   (1) 11-(3-methylene-4-oxo-2-oxetano)-3,5,7-trimethyl-2,4-undecadienoic acid; and
   (2) methyl 11-(3-methylene-4-oxo-2-oxetano)-3,5,7-trimethyl-2,4-undecadienoate.

One further embodiment of the compounds of the present invention is the class of compounds of the formula (I) wherein R$^1$ is COR$^4$ and R$^4$ is amino, C$_{1-6}$ alkylamino, substituted C$_{1-6}$ alkylamino, phenylamino or substituted phenylamino. A specific sub class of this embodiment are the compounds of the formula (I) wherein R$^2$ is hydroxy. Exemplifying this sub class are the following compounds:
   (1) 11-(3-hydroxymethyl-4-oxo-2-oxetano)-3,5,7-trimethyl-2,4-undecadienamide;
   (2) N-n-hexyl 11-(3-hydroxymethyl-4-oxo-2-oxetano)-3,5,7-trimethyl-2,4-undecadienamide;
   (3) N-(4-bromophenyl) 11-(3-hydroxymethyl-4-oxo-2-oxetano)-3,5,7-trimethyl-2,4-undecadienamide; and
   (4) N-(2-hydroxyethyl) 11-(3-hydroxymethyl-4-oxo-2-oxetano)-3,5,7-trimethyl-2,4-undecadienamide.

Another embodiment of the compounds of the present invention is the class of compounds of the formula (I) wherein R$^2$ is C alkoxy, C$_{2-6}$ alkenyloxy or anisyldiphenylmethyloxy. A specific sub class of this embodiment are the compounds of the formula (I) wherein R$^1$ is COR$^4$ and R$^4$ is hydroxy or C$_{1-6}$ alkoxy. Exemplifying this sub class are the following compounds:
   (1) methyl 11-(3-methoxymethyl 4-oxo-2-oxetano)-3,5,7-trimethyl-2,4-undecadienoate;
   (2) methyl 11-(3-ethoxymethyl 4-oxo-2-oxetano)-3,5,7-trimethyl-2,4-undecadienoate;
   (3) methyl 11-[3-(2-propenyloxymethyl)-4-oxo-2-oxetano]-3,5,7-trimethyl-2,4-undecadienoate;
   (4) 11-(3-methoxymethyl-4-oxo-2-oxetano)-3,5,7-trimethyl-2,4-undecadienoic acid;
   (5) 11-(3-anisyldiphenylmethyloxymethyl-4-oxo-2-oxetano)-3,5,7-trimethyl-2,4-undecadienoic acid; and
   (6) diphenylmethyl 11-(3-methoxymethyl-4-oxo-2-oxetano)-3,5,7-trimethyl-2,4-undecadienoate.

Another embodiment of the compounds of the present invention is the class of compounds of the (I) wherein R$^2$ is formyloxy, C$_{1-6}$ alkylcarbonyloxy, carboxy C$_{1-6}$ alkylcarbonyloxy, aminocarbonyloxy and C$_{1-6}$ alkylaminocarbonyloxy. A specific sub class of this embodiment are the compounds of the formula (I) wherein R$^1$ is COR$^4$ and R$^4$ is C$_{1-6}$ alkoxy. Exemplifying this sub class are the following compounds:
   (1) methyl 11-(3-formyloxymethyl-4-oxo-2-oxetano)-3,5,7-trimethyl-2,4-undecadienoate;
   (2) methyl 11 [3-(3 -carboxypropionyloxymethyl)-4-oxo-2-oxetano]-3,5,7-trimethyl-2,4-undecadienoate;
   (3) methyl 11-(3-urethanylmethyl)-4-oxo-2-oxetano)-3,5,7-trimethyl-2,4-undecadienoate;

(4) methyl 11-[3-(N-methylurethanylmethyl)-4-oxo-2-oxetano]-3,5,7 trimethyl-2,4-undecadienoate; and
(5) methyl 11-[3-(2-methylbutyryloxymethyl)-4-oxo-2-oxetano]-3,5,7-trimethyl-2,4-undecadienoate.

Also illustrative of the compounds of the present invention are the following compounds of the formula (I):
(1) methyl 11-(3-methanesulfonyloxymethyl-4-oxo-2-oxetano)-3,5,7-trimethyl-2,4-undecadienoate;
(2) 2-pyridyl 11-(3-hydroxymethyl-4-oxo-2-oxetano)-3,5,7-trimethyl-2,4-undecadienthioate; and
(3) tert-butyl 11-(3-hydroxymethyl-4-oxo-2-oxetano)-3,5,7-trimethyl-2,4-undecadienoate.

One additional embodiment of the compounds of the present invention is the class of compounds of the formula (I) wherein A is $C_{6-17}$ alkylene. Exemplifying this embodiment are the following compounds:
(1) E-3-methyl-4-(5-phenylpentyl)-2-oxetanone
(2) E-3-methyl-4-(6-phenylhexyl)-2-oxetanone
(3) E-3-methyl-4-(9-phenylnonyl)-2-oxetanone
(4) E-3-methyl-4-decyl-2-oxetanone A further embodiment of the compounds of the present invention is the class of compounds of the formula (I) wherein A is substituted $C_{6-17}$ alkylene. Exemplifying this embodiment are the following compounds:
(1) 8-(3-hydroxymethyl-4-oxo-2-oxetanyl)-4-methyl-2-octanone
(2) 8-(3-hydroxymethyl-4-oxo-2-oxetanyl)-4-methyl-2-(4-bromophenylhydrazono)octane
(3) 8-(3-methoxymethyl-4-oxo-2-oxetanyl)-4-methyl-2-octanone
(4) 8-(3-methoxymethyl-4-oxo-2-oxetanyl)-4-methyl-2-methoxyoctane
(5) 8-(3-methoxymethyl-4-oxo-2-oxetanyl)-4-methyl-2-octanol
(6) E-3-methyl-4-(9-oxodecyl) 2-oxetanone.

A further embodiment of the compounds of the present invention is the class of compounds of the formula (I) wherein A is monounsaturated $C_{6-17}$ alkylene. Exemplifying this embodiment is the following compound:
(1) E-3-methyl-4-(9-decenyl)-2-oxetanone.

A still further embodiment of the compounds of the present invention is the class compounds of the formula (I) wherein A is substituted monounsaturated $C_{6-17}$ alkylene. Exemplifying this embodiment are the following compounds:
(1) methyl 11-(3-hydroxymethyl-4-oxo-2 oxetanyl)-4,5-oxiranyl-3,5,7 trimethyl-2-undecenoate
(2) 11-(3-hydroxymethyl-4-oxo-2 oxetanyl)-4,5-oxiranyl-3,5,7-trimethyl-2-undecenoic acid
(3) methyl 11-(3-hydroxymethyl-4-oxo-2-oxetanyl)-4,5-dihdroxy-3,5,7-trimethyl-2-undecenoate
(4) methyl 11-(3-methoxymethyl-4-oxo-2-oxetanyl)-4,5-dihdroxy-3,5,7-trimethyl-2-undecenoate The present invention is also directed to a method of treating the potentially serious and life threatening effects of ketoacidosis, and in particular diabetic ketoacidosis which comprises the administration to a subject in need of such treatment a nontoxic therapeutically effective amount of a compound represented by the general structural formula (I) and pharmaceutically acceptable salts thereof.

Specifically the compounds of this invention may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 20 mg to 2000 mg (preferably 20 to 100 which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

One compound of above structural Formula I, wherein $R_1$ is $—COR^4$ and $R^4$ is hydroxy, $R_2$ is hydroxy, $R_3$ is hydrogen, the broken line represents a connecting single bond and $\phi$ is

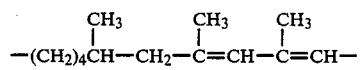

and which has the structural Formula II

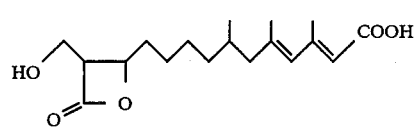

and is identified as 12-hydroxy-13-hydroxymethyl-3,5,7-trimethyl tetradeca-2,4-dien-1,14, dioic acid 12,14 lactone. This compound in particular has been found to possess significant activity in reducing ketoacidosis as measured by the control of acetoacetate and $\beta$-hydroxy butyrate levels in blood.

To test the effect of Compound II a protocol was developed to assay for serum ketone bodies in mice. Where indicated, animals were fasted for 24 hours in order to induce plasma acetoacetate and $\beta$-hydroxy butyrate. The mice were administered Compound II by stomach tube as a suspension in 2.5% emulphor at the indicated concentration. Animals not given Compound II were administered a solution containing only 2.5% emulphor. After 90 minutes, the animals were bled by intraorbital injection, the blood was deprotenized immediately with perchloric acid and this solution neutralized with potassium bicarbonate. A sample of this extract was incubated with either NAD or NADH and $\beta$-hydroxybutyrate dehydrogenase for determination of $\beta$-hydroxybutyrate and acetoacetate, respectively.

Ketone bodies in the treated animals were compared to fed and fasted control animals. The results are shown in the following tables.

TABLE 1

| Effect of Compound II on Ketone Bodies in Mouse Blood | | | |
|---|---|---|---|
| Treatment | Acetoacetate | (nmols/ml) $\beta$-hydroxy-butyrate | Total Ketones |
| Fed | 88 ± 15 | 126 ± 27 | 214 ± 42 |
| Fasted | 376 ± 24 | 984 ± 63 | 1360 ± 87 |
| Fasted + Compound II at 12.5 mg/kg | 110 ± 19 | 171 ± 11 | 281 ± 29 |
| Fasted + Compound II at 25 mg/kg | 61 ± 11 | 82 ± 8 | 143 ± 19 |

Compound II suppressed the rise in ketone bodies which is usually induced in fasting animals There was a dose response effect with 25 mg/kg reducing the ketone bodies to about one-half of that at 12.5 mg/kg.

In another experiment, fasted mice were given Compound II orally at 25 mg/kg and the blood ketones evaluated after 1, 2 and 3 hrs. These results are described in Table 2.

Ketone bodies from fasted and the fasted animals treated with were similar at zero time. At one hr, Compound II reduced the ketones greater than two-fold to almost that seen in the fed controls and they remained low during the three hr period of this experiment. During this period fasted levels remained elevated.

TABLE 2

Effect of Compound II on Total Ketone Bodies in Mouse Blood

| Treatment | Total Ketone Bodies[a] (nmoles/ml) Time | | | |
|---|---|---|---|---|
| | 0 | 1 hr | 2 hr | 3 hr |
| 1. Fed[b] | 142 + 19 | 163 + 61 | 120 + 33 | 260 + 86 |
| 2. Fasted[b] | 470 + 88 | 511 + 147 | 672 + 77 | 567 + 154 |
| 3. Fasted + Compound II | 597 + 51 | 214 + 56 | 221 + 109 | 116 + 30 |

[a]sum of acetoacetate and β-hydroxybutyrate
[b]animals given an equivalent of 2.5% emulphor solution without Compound II The compounds of this invention wherein $R^4$ is hydroxy or $C_{1-6}$ alkoxy and $R^2$ is hydroxy are conveniently prepared as described in *J. Chem. Soc. (C)*, 1971 3888–3891 by the fermentation of an identified fungus ACC 1233 and the standard chemical transformations disclosed therein. These compounds wherein $R^1$ is hydroxy may also be prepared by the cultivation of a member of the class of fungi selected from ATCC 20788, ATCC 20789 or ATCC 20790 followed by a standard isolation.

The morphological characteristics of the microorganisms ATCC 20788, ATCC 20789, and ATCC 20790 are described below:

*Fusarium* sp. MF5045 ATCC 20788

Cultural Characteristics

On Czapek Dox agar—mycelia is extensive, white and cottony, becoming felted and white with sectors of faint bluish green tinge or a pale peach tinge as culture ages. Moist areas faint bluish-green in color develop where macroconidia are abundant.

On potato dextrose agar—mycelia is extensive, white and cottony, becoming felted and pinkish-tan in color as culture ages. When vegetative inoculum is used, moist areas, tan in color, develop where macroconidia are abundant.

On Sabouraud-maltose agar—mycelia is extensive, velvety and white with peach to light purple tinge.

Morphological Characteristics

Microconidia are generally unicellular, oval ellipsoidal, borne singly and held in a gelatinous mass. 1.8–2.4 m × 3.6 to 4.8 m.

Macroconidia are 3 to 5 celled, thin-walled, ends are tapered and slightly curved. 3.6–4.8 m × 24–36 m.

Chlamydospores are abundant, terminal and intercalary, globose, generally smooth walled, usually formed singly but sometimes formed in pairs.

*Fusarium* sp. MF5058 ATCC 20789

Cultural Characteristics

On Czapek-Dox agar—mycelia is extensive, white and cottony, becoming felted and white with sectors of a faint bluish-green tinge or a pale peach tinge as culture ages. Moist areas faint bluish green in color develop where macroconidia are abundant.

On potato-dextrose agar—mycelia is extensive, white and cottony, becoming felted and pinkish-tan in color as culture ages. When vegetative inoculum is used, moist areas, tan in color develop where macroconidia are abundant.

On Sabouraud maltose agar—mycelia is extensive, velvety and white with peach to light purple tinge.

Morphological Characteristics

Microconidia are generally unicellular, oval-ellipsoidal, borne singly and held in a gelatinous mass. 1.8–2.4μ × 3.6–4.8μ.

Macroconidia are 3 to 5 celled, thin-walled, ends are tapered and slightly curved 3.6–4.8μ × 24–36μ.

Chlamydospores are abundant, terminal and intercalary, globose, generally smooth walled, usually formed singly but sometimes formed in pairs.

*Fusarium* sp. MF 5084 ATCC 20790

Cultural Characteristics

On Czapek-Dox agar—mycelia is extensive, white and cottony, becoming felted and white with sectors of a faint bluish-green tinge or a pale peach tinge as culture ages. Moist areas faint bluish-green in color develop where macroconidia are abundant.

On potato dextrose agar—mycelia is extensive, white and cottony, becoming felted and pinkish tan in color as culture ages. When vegetative inoculum is used, moist areas, tan in color, develop where macroconidia are abundant.

On Sabouraud maltose agar—mycelia is extensive, velvety and deep-pinkish tan in color. Vegetative growth and medium become purplish red.

Morphological Characteristics

Microconidia are generally unicellular, oval-elliposoidal, borne singly and held in a gelatinous mass 1.8–2.4μ × 3.6–4.8μ.

Macroconidia are 3 to 5 celled, thin-walled, ends are tapered and slightly curved. 3.6–4.8μ × 24–36 μ.

Chlamydospores are abundant, terminal and intercalary, globose, generally smooth-walled formed singly but sometime formed in pairs.

The compound of the formula (I) wherein $R^1$ is hydroxy and $R^2$ is hydrogen may be produced by the cultivation of a member of the class of fungi ATCC 20788, ATCC 20789, or ATCC 20790 under the following general conditions.

A preserved source of the culture is used to inoculate an agar slant containing a nutrient medium for growth. After incubation at room temperature for 1 to 5 weeks a portion of this growth is used to inoculate a liquid nutrient medium containing sources of carbon, nitrogen, phosphorus and other elements necessary for life. This medium is incubated at 25° to 30° C., usually 28°. The flask containing the culture and liquid nutrient medium is incubated with or without agitation on a rotary shaker from 0 to 400 RPM, most often at 212 RPM. After 1 to 10 days, when growth is abundant, usually between 2 and 4 days, the culture growth is used to inoculate a flask containing a medium which supports production of the product. Such production media contain carbon sources such as corn, glycerol, corn oil, dextrose, cod oil or peanut meal, nitrogen and sulfur sources such as yeast extract, corn steep liquor, corn, lard water, peanut meal, soy flour, tomato paste and the like as well as organic and inorganic ions such as potassium, phosphorous, calcium, tartrate, iron and magnesium. These production media are inoculated with the culture growth and are incubated at from 20° to 30° most often 25° for 3 to 30 days usually 7–14 days with or without agitation.

The compound of the formula (I) wherein $R^4$ is hydroxy may be recovered from the fermentation medium by extraction with a water miscible solvent, such as $C_{1-3}$ alcohol, especially methanol and water in a ratio from 0.1:1.0 to 1.0 to 0.1, especially 1:1 by volume. The extract is portioned between the aqueous phase and a water miscible organic solvent such as ethyl acetate or methylene chloride. The desired compound is further purified by chromatography on silica gel and then Sephadex LH20 (tradename for dextran derivatives used as gel filtrants in organic solvents, manufactured by Pharmacia Fine Chemicals, Inc.). Finally, the product may be crystallized from aqueous alcohol.

The compounds of the formula (I) wherein $R^4$ is amino, $C_{1-6}$ alkylamino, substituted $C_{1-6}$ alkylamino, phenylamino or substituted phenylamino are conveniently prepared from the appropriately substituted compound of the formula (I) wherein $R^4$ is hydroxy by the formation of a mixed anhydride followed by the addition of the appropriately substituted amine or ammonia.

The compounds of the formula (I) wherein $R^2$ is $C_{1-6}$ alkoxy, $C_{2-6}$ alkenyloxy or anisyldiphenylmethyloxy are conveniently prepared from the appropriately substituted compound of the formula (I) wherein $R^2$ is hydroxy and $R^4$ is alkoxy, substituted alkoxy, amino, alkylamino, substituted alkylamino, phenylamino or substituted alkylamino by reaction with the appropriate diazo compounds. If the free acid of the formula (I) ($R^4$ is hydroxy) is desired the appropriately substituted ester is hydrolyzed under mild conditions subsequent to the treatment with the diazo compound. In an alternate process these compounds can be prepared by the reaction of the appropriate alkylhalide or alkenylhalide in the presence of silver oxide.

The compounds of the formula (I) wherein $R^2$ is formyloxy, $C_{1-6}$ alkoxycarbonyloxy, carboxy $C_{1-6}$ alkoxycarbonyloxy, aminocarbonyloxy and $C_{1-6}$ alkyl aminocarbonyloxy are conveniently prepared from the compounds of the formula (I) wherein $R^2$ is hydrogen by the reaction with either an anhydride, acylchloride or an isocyanate.

The compounds of the formula (I) wherein $R^2$ is hydrogen or halogen and the broken line is a connecting single bond are conveniently prepared from the appropriately substituted compound of the formula (I) wherein $R^4$ and $R^2$ are hydroxy and the broken line is a connecting single bond by the formation of the $C_{1-6}$ alkyl ester analog followed by the replacement of the hydroxy moiety with a halogen to give the halo ethyl derivative, $R^2$ is halogen, which can then reduced with tributyltin hydride to yield the compounds of the formula (I) wherein $R^2$ is hydrogen. If the free acid of the formula (I) ($R^4$ is hydroxy) is desired the ester function is removed under mild hydrolytic condition either before reduction for the compounds of the formula (I) wherein $R^2$ is halogen or after reduction for the compounds of the formula (I) wherein $R^2$ is hydrogen.

The compounds of the formula (I) wherein $R^2$ is cyano are conveniently prepared from the appropriately substituted compound of the formula (I) wherein $R^2$ is hydroxy and $R^4$ is alkoxy and the broken line is a connecting single bond by forming the methanesulfonyloxy derivative and then displacing the methanesulfonyloxy group with a cyano anion from an alkali metal cyanide, such as sodium cyanide. If the free acid of the formula (I) ($R^4$ is hydroxy) is desired the appropriately substituted ester is hydrolyzed under mild conditions.

The compounds of the formula (I) wherein $R^2$ is azido are conveniently prepared from the compounds of the formula (I) wherein $R^2$ is methanesulfonyloxy by the reaction with an alkali metal azide, such as sodium azide or from compounds of the formula (I) wherein $R^2$ is hydroxy by reaction with an alkali metal azide, triphenylphosphine and dialkoxycarbonylazodicarboxylate.

The compounds of the formula (I) wherein $R^2$ is $C_{1-6}$ alkylcarbonylthio are conveniently prepared from the compounds of the formula (I) wherein $R^2$ is methanesulfonyloxy by the reaction with an alkali metal thiolcarboxylate, such as potassium thiolacetate or from the compounds of the formula (I) wherein $R^2$ is hydroxy by reaction with an alkali metal thiolcarboxylate, triphenylphosphine and a dialkoxycarbonylazodicarboxylate.

The compounds of the formula (I) wherein the broken line is a connecting double bond are readily prepared by the elimination of the methanesulfonyloxy group from the appropriately substituted derivatives of the compounds of the formula (I) under mild basic conditions.

When $R^1$ is hydrogen or phenyl and A is not substituted with an oxo, an epoxy or a 4 bromophenyl hydrazono, the compounds of the formula (I) wherein $R^2$ is hydrogen, that is the 3-methyl-4-substituted 2-oxetanones, are conveniently prepared from readily available starting materials as described in the following synthetic pathway:

$CH_3CO_2Et + R^1ACHO \longrightarrow$ (1)

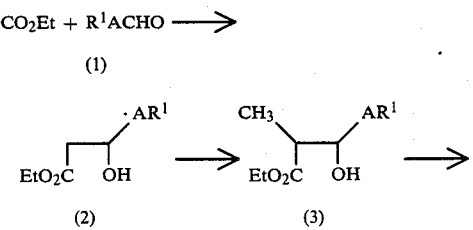

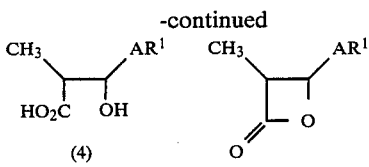

(I) wherein R² is hydrogen

Ethyl acetate is reacted with an appropriately substituted aldehyde (1) wherein R¹ is hydrogen or phenyl and A is not substituted with an oxo, epoxy or 4-bromophenylhydrazono in the presence of two moles of lithium diisopropylamide to the β-hydroxy ester (2) in its dianion form. The dianion is alkylated with methyl iodide to give the β-hydroxy ester. Base hydrolysis of the B hydroxy ester (3) to yield (4) is followed by a standard lactonization to give the compounds of the formula (I) wherein R² is hydrogen. When A is substituted with an oxo, an epoxy or a 4-bromophenylhydrazono, a mono or diunsaturated is further elaborated by a selective bromination dehydrobromination followed by oxidation to the oxo substituted compounds which are transformed to the epoxy substituted and 4-bromophenylhydrazono substituted compounds under standard reaction conditions.

The compounds of the formula (I) wherein R² is hydroxy or $C_{1-6}$ alkoxy are conveniently prepared from the known Compound II or its alkyl ester according to the following synthetic transformations. When A is substituted with an epoxy group, Compound II or its $C_{1-6}$ alkyl ester is reacted with m-chloroperbenzoic acid. When A is substituted with a geminal dihydroxy group, Compound II or its $C_{1-6}$ alkyl ester is reacted with osmium tetroxide. When A is substituted with an oxo group the 13-$C_{1-6}$ alkoxymethyl derivative of Compound II is reacted with ozone. The 13-$C_{1-6}$ alkoxymethyl derivatives may be prepared by the alkylation of the hydroxymethyl group with an alkyl halide in the presence of silver oxide. The oxo substituted compounds can be converted into the $C_{1-6}$ alkoxy substituted compounds by reduction to the hydroxy followed by an alkylation under standard conditions. The oxo compound can also be converted into the 4-bromophenylhydrazono compound using standard reaction conditions.

The following examples illustrate the preparation of the compounds and their incorporation into pharmaceutical compositions and as such are not to be construed as limiting the invention set forth in the claims appended hereto.

The composition of media employed in the examples are listed below. Media are prepared in a 250 ml Erlenmeyer flask. The contents are sterilized with steam at 121° C., 20 pounds pressure for 20 minutes. Media that contain corn are rehydrated and again sterilized with steam at 121° C., 20 pounds pressure for 20 minutes before inoculation.

| Medium | Composition |
| --- | --- |
| F867 | 10 g/flask corn, 0.1 g/flask MgSO₄.7H₂O, .01 g/flask FeSO₄.7H₂O, 15 ml/flask of (33 g/l yeast extract) after 7 days incubation add 20 ml H₂O/flask, incubate without agitation for 14 days |
| F870 | 10 g/flask corn, .01 g/flask FeSO₄.7H₂O, .01 g/flask ZnSO₄.7H₂O, 15 ml/flask of (33 g/l yeast extract), incubate without agitation for 14 days |
| F872 | 10 g/flask corn, 15 ml/flask of (33 g/l yeast extract) incubate without agitation for 7 days then at 220 rpm for 7 days |
| F848 | 10 g/flask corn, 15 ml/flask of (MgSO₄.7H₂O 0.1 g/l, Na tartrate 0.1 g/l, FeSO₄.7H₂O 0.01 g/l, ZnSO₄.7H₂O 0.01 g/l) incubate at 220 rpm for 7 days |
| KF | Corn Steep 5 g<br>Tomato Paste 40 g<br>Oat Flour 10 g<br>Dextrose 10 g<br>Distilled water 1000 ml<br>Trace Element Mix No. 2–10 ml of (FeSO₄.7H₂O 1 g/l, MnSO₄.4H₂O 1 g/l, CuCl₂.2H₂O 25 mg/l, CaCl₂.2H₂O 100 mg/l, H₃BO₃ 56 mg/l, (NH₄)₆Mo₇O₂₄.4H₂O 19 mg/l, ZnSO₄.7H₂O 200 mg/l Deionized water 1000 ml) pH 6.8 |
| YME | Yeast extract 4 g<br>Malt extract 10 g<br>Dextrose 4 g<br>Agar 20 g<br>pH 7<br>Distilled water 1000 ml |

EXAMPLE 1

Preparation of 12-Hydroxy-13-hydroxymethyl-3,5,7-trimethyltetradeca-2,4-dien-1,14--dioic acid 12,14 lactone (a) Fermentation of ATCC 20790

A culture of ATCC 20790 was inoculated onto YME slant medium. After growth at 25° C., a portion of this slant was used to inoculate a baffled 250 ml Erlenmeyer flask containing KF growth medium (54 ml). The flask was incubated with agitation at 212 rpm on a rotary shaker (2 inch throw) for 3 days at 28° C. Then a portion of the growth (2 ml) was used to inoculate an unbaffled 250 ml Erlenmeyer flask containing Medium F867 (media F870 or F872 may also be employed). After 14 days incubation at 25° C. methanol (20 ml) was added and then let stand overnight. Then water (10 ml) was added to the flask The desired product was contained in the aqueous methanol extract.

(b) Fermentation of ATCC 20789

(1) A preserved culture source of ATCC 20789 was used to inoculate a baffled 250 ml Erlenmeyer containing KF growth medium (54 ml). The flask was incubated with agitation at 212 rpm on a rotary shaker (2 inch throw) for 3 days at 28° C. Then a portion of the growth (2 ml) was used to inoculate an unbaffled 250 ml Erlenmeyer flask containing medium F870. After 14 days incubation at 25° C., 50 percent aqueous methanol was added. The aqueous methanol extract was employed in the isolation and purification procedure described below.

(c) Fermentation of ATCC 20788

A culture of ATCC 20788 was used to inoculate a baffled 250 ml Erlenmeyer flask containing KF growth medium (54 ml). The flask was incubated with agitation at 212 rpm on a rotary shaker (2 inch throw) for 3 days at 28° C. Then a portion of the growth (2 ml) and remaining medium was used to inoculate an unbaffled 250 ml Erlenmeyer flask containing medium F848. After 7 days incubation at 25° C., the contents of the flask were extracted with methanol (20 ml) in water (10 ml) to obtain the desired product.

(d) Isolation and Purification

The aqueous methanol extracts (700 ml each) from the fermentation medium from two series of fermentations of the microorganism ATCC 20789 according to the general procedure of Example 1(b) were filtered. The first extract was partitioned with methylene chloride (700 ml) and the second extract was partitioned with ethyl acetate (700 ml). In both cases activity was located in the organic phase. The two organic phases were combined and concentrated in vacuo. The residue was dissolved in ethyl acetate/hexane (4:6) (2 ml) and chromatographed on silica gel (200 ml eluted with a step gradient of ethyl acetate:hexane (4:6, 6:4, 5:5 and 7:3). The desired product was rechromatographed on LH-20 (20 ml) eluted with methylene chloride:hexane:methanol (10:10:1) and the desired product eluted from the column with methanol. An analytically pure sample of the title compound was a crystalline compound mp. 76°–77° C.

The $^{13}C$ NMR spectrum was recorded in $CD_3OD$ at ambient room temperature (25 mg/0.4 ml) on a Varian XL 400. Chemical shifts are given in ppm downfield of tetramethylsilane relative to the solvent peak at 49.0 ppm as standard. In agreement with the mass spectral data, 18 carbon atoms are observed with the following chemical shifts: 18.5, 19.8 (2X), 26.4, 27.8, 32.0, 35.0 37.8, 49.9, 58.0, 60.0, 76.3, 118.7, 130.6, 142.3, 155.7, 170.4, 171.9 ppm.

Mass Spectrum Calc'd for $C_{18}H_{28}O_5+H$: 325.201. Found 325.201.

EXAMPLE 2

Preparation of Methyl 12-hydroxy-13-hydroxymethyl-3,5,7-trimethyltetradeca-2,4-dien-1,14-dioic acid 12,14 lactone To a stirred solution of the compound from Example 1(d) (32 mg, 0.01 mmol) in anhydrous diethyl ether (0.5 ml) at ambient temperature was added dropwise, diazomethane dissolved in anhydrous diethyl ether until the reaction mixture maintained a bright yellow color. The excess diazomethane was removed by bubbling nitrogen through the reaction mixture. The desired product was purified by preparative thin layer chromatography on silica gel eluted with 1 percent methanol in methylene chloride to afford above titled compound as an oil.

IR spectrum max 3520, 1820, 1705 $cm^{-1}$.
Mass Spectrum Calc'd for $C_{19}H_{30}O_5$ 338. Found: 338.

EXAMPLE 3

Preparation of 12-Hydroxy-13-hydroxymethyl-3,5,7-trimethyltetradecan-1,14-dioic acid 12,14 lactone To a solution of the compound from Example 1(d) (32 mg, 0.01 mmol) in glacial acetic acid (0.5 ml) was added platinum oxide (2 mg) and the compound was hydrogenated at ambient temperature under atmospheric pressure. After one hour, the flask was flushed with nitrogen and the reaction mixture filtered. The filtrate was concentrated in vacuo. The residue was purified by preparative thin layer chromatography on silica gel, eluted with 3 percent methanol in methylene chloride to afford the above titled compound as an oil.

IR spectrum max 1820, 1710 $cm^{-1}$.
Mass spectrum Calc'd for $C_{18}H_{30}O_4$ ($M-H_2O$): 310. Found: 310.

EXAMPLE 4

Preparation of Alkali and Alkaline Earth Salts of Compound I wherein $R^4$ is hydroxide To a solution of the lactone from Example 1 (42 mg) in ethanol (2 ml) is added aqueous NaOH (1 equivalent). After one hour at room temperature, the mixture is taken to dryness in vacuo to yield the sodium salt of Compound I, wherein R is hydrogen.

In like manner, the potassium salt is prepared using one equivalent of potassium hydroxide, and the calcium salt using one equivalent of CaO.

EXAMPLE 5

As a specific embodiment of an oral composition of a compound of this invention, 20 mg of the lactone from Example 1 is formulated with sufficient finely divided lactose to provide a total amount of 580 to 590 mg to fill a size 0 hard gelatin capsule.

EXAMPLE 6

As a specific embodiment of a parenteral composition of a compound of this invention, 20 mg of the lactone from Example 1, as the sodium salt, is dissolved in sterile water, buffered to a pH of 7 with 1.0 mM potassium phosphate buffer solution to a concentration of 2.0 percent and is placed in a sterile ampule for parenteral administration.

EXAMPLE 7

Preparation of N-n-hexyl 11-(3-hydroxymethyl-4-oxo-2-oxetano)-3,5,7-trimethyl-2,4-undecadienamide To a solution of the compound from Example 1 (d) (102 mg, 0.3 mmole) in methylene chloride (1 ml) and tetrahydrofuran (14 ml) containing N-methylmorpholine (35 mg, 0.34 mmole) at $-20°$ to $-25°$ C. was added isobutyl chloroformate (46 mg, 0.34 mmole) during 10 minutes. To this mixed anhydride mixture at $-25°$ was then added dropwise a solution of n-hexylamine (76 mg, 0.75 mmole) in tetrahydrofuran (0.5 ml). After the addition, the mixture was kept at $-20°$ to $-25°$ for 1 hour and raised to room temperature slowly over a 2 hour period and stirred at room temperature overnight. The reaction mixture was concentrated in vacuo and the residue was purified via preparative TLC using silica gel plates and developed with 6% methanol in methylene chloride to afford the desired product as an oil.

Mass spectrum m/e 407 ($M^+$); 200 MHz NMR ($CDCl_3$): δ 0.84 (t, 3H, $CH_3$—), 3.28 (9, 2H, —$NHCH_2$—), and 5.57 ppm (t, 1H, CO—NH—).

EXAMPLE 8 TO 10

Utilizing the general procedure described in Example 7 the following compounds were prepared from the compound from Example 1(d) and an equivalent amount of the appropriate amine.

| Compound No. | Name | MS | 200 MHz NMR |
|---|---|---|---|
| 8 | 11-(3-hydroxymethyl-4-oxo-2-oxetano)-3,5,7-trimethyl-2,4-undecadienamide | | 5.38 ppm (s, 2H) |
| 9 | N—(4-bromophenyl)- | 477.479 | 7.47 ppm |

-continued

| Compound No. | Name | MS | 200 MHz NMR |
|---|---|---|---|
|  | 11-(3-hydroxymethyl-4-oxo-2-oxetano)-3,5,7-trimethyl-2,4-undecadienamide |  | (AB pattern, 4H) 5.32 |
| 10 | N-(2-hydroxyethyl)-11-(3-hydroxymethyl-4-oxo-2-oxetano)-3,5,7-trimethyl-2,4-undecadienamide | 368 (M$^+$ + H) |  |

EXAMPLE 11

Preparation of methyl 11-(3-methoxymethyl-4-oxo-2oxetano)-3,5,7-trimethyl-2,4-undecadienoate

Method A

To a solution of the compound from Example 2 (20 mg) in diethyl ether (15 ml) in the presence of trifluoroboron etherate (1 drop) at 0° to 5° C. was added large excess of diazomethane ether solution until the discoloration became very slow. The resulting solution was concentrated and purified via preparative TLC using silica gel plate and developed with 3% ethyl acetate in methylene to yield the desired product as an oil. 200 MHz NMR CDCl$_3$): 3.38 ppm (CH$_3$OCH$_2$—).

Method B

To a solution of the compound from Example 1(d) (200 mg) in diethyl ether (30 ml) in the presence of trifluoroboron etherate (5 drops) at 0° to 5° C. was added large excess of diazomethane ether solution. The reaction mixture was concentrated and purified as in Method A to give the desired product.

Method C

To a solution of the compound from Example 1(d) (300 mg) in diethyl ether (10 ml) was added methyl iodide (5 g) and commercial silver oxide (0.4 g). The mixture was stirred at room temperature for 3 days and added methyl iodide (1 g) and silver oxide (0.5 g) daily during this period. The mixture was filtered and concentrated. The residue was purified via flash column chromatography to give the desired product.

EXAMPLE 12

Preparation of methyl 11-(3-ethoxymethyl-4-oxo-2-oxetano)-3,5,7-trimethyl-2,4-undecadienoate To a solution of the compound from Example 2 (12 mg) in diethyl ether (0.5 ml) was added ethyl iodide (400 mg) and silver oxide (80 mg). The mixture was capped tightly and stirred at 48° to 50° for 60 hours. The resulting mixture was purified via preparative TLC to give the desired product. 200 MHz NMR: 2.20 (t, 3H, CH$_3$CH$_2$O) and 3.56 ppm (9, 2H, CH$_3$CH$_2$O).

EXAMPLE 13

Preparation of methyl 11-[3-(2-propenyloxymethyl)-4-oxo-2-oxetano]-3,5,7-trimethyl-2,4-undecadienoate Utilizing the general procedure of Example 12 but employing alkyl chloride in place of ethyl iodide the desired product was obtained. 200 MHz NMR 4.04 ppm (m, 2H) 5.3 ppm (m, 2H) and 5.9 ppm (m, H).

EXAMPLE 14

Preparation of 11-(3-methoxymethyl-4-oxo-2-oxetano)-3,5,7-trimethyl-2,4-undecadienoic acid Step A: Preparation of Diphenylmethyl 11-(3-hydroxymethyl-4-oxo-2-oxetano)-3,5,7-trimethyl-2,4-undecadienoate To a solution of the compound from Example 1(d) (324 mg, 1.0 mmole) in diethyl ether (10 ml) was added diphenyl diazomethane (230 mg, 1.2 mmole). The mixture was stirred at room temperature for 2 days until complete disappearance of the starting material by TLC. The desired intermediate was isolated via preparative TLC purification 200 MHz NMR: 6.96 (s, 1H, Ph$_2$CH—OOO) and 7.22–7.44 ppm (m, 10H, ArH).

Step B: Preparation of Diphenylmethyl 11-(3-methoxymethyl-4-oxo-2-oxetano)-3,5,7-trimethyl-2,4-undecadienoate To a solution of the compound from Step A (50 mg, 0.1 mmole) in diethyl ether (0.5 ml) was added methyl iodide (720 mg, 5.0 mmole) and silver oxide (100 mg, 0.43 mmole). The mixture was capped tightly and heated at 45°–50° with stirring for 18 hours. The mixture was filtered, and the filtrate was purified via preparative TLC using silica gel plates and developed with 5% ethyl acetate in methylene chloride to yield the desired intermediate. 200 MHz NMR: 3.39 ppm (s, 3H, CH$_3$OCH$_2$).

Step C: Preparation of 11-(3-methoxymethyl 4-oxo-2-oxetano)-3,5,7-trimethyl-2,4-undecadienoic Acid To a solution of the compound from Step B (20 mg) and anisole (150 mg) in methylene chloride (2 ml) at 0° to 5° C. was added a solution of 10% trifluoroacetic acid in methylene chloride (0.2 ml). The mixture was stirred at ambient temperature for 1 hour and purified via preparative TLC to give the desired product. IR (CHCl$_3$): 1814 cm$^{-1}$; mass spectrum (FAB) m/e 339 (M$^+$+H); 200 MHz NMR: in accord with the structure.

EXAMPLE 15

Preparation of 11-(3-anisyldiphenylmethyloxymethyl-4-oxo-2-oxetano)-3,5,7-trimethyl-2,4-undecadienoic acid To a solution of the compound from Example 1(d) (100 mg) in pyridine (1.5 ml) was added anisyldiphenylmethyl chloride (113 mg). The mixture was stirred at room temperature for 17 hours, and pumped to dryness. The residue was purified via preparative TLC using silica gel plates and developed with 5% methanol in methylene chloride to give the desired product. 200 MHz NMR 3.80 (s, 3H, CH$_3$O$\phi$) and 7.2–7.5 ppm (m, 14H, ArH).

EXAMPLE 16

Preparation of methyl 11-(3-methanesulfonyloxymethyl-4-oxo-2-oxetano)-3,5,7-trimethyl-2,4-undecadienoate To a solution of the compound from Example 2 (100 mg) and triethylamine (150 mg) in methylene chloride (5 ml) at 0° to 5° was added a solution of methanesulfonyl chloride (150 mg) in methylene chloride (0.5 ml) during 10 minutes. The mixture was stirred at 0° to 5° for ½ hour and then at room temperature for ½ hour. The desired product was isolated via preparative TLC purification. 200 MHz NMR 3.08 ppm (s, 3H, $CH_3SO_3$—).

EXAMPLE 17

Preparation of methyl 11-(3-formyloxymethyl-4-oxo-2-oxetano)-3,5,7-trimethyl-2,4-undecadienoate Diethyl azidocarboxylate (0.04 ml, 2 eg) was added dropwise to a stirred solution of the compound from Example 2 (0.034 g, 0.1 mmol) triphenylphosphine (0.053 g, 0.2 mmol), and formic acid (0.01 ml, 2.7 eg) in anhydrous tetrahydrofuran (0.6 ml) at ambient temperature. After one hour, at ambient temperature the reaction mixture was evaporated in vacuo and purified by preparative thin layer chromatography on silica gel eluted with ethyl acetate: hexane (30:70) to afford the desired product as a viscous gum.

EXAMPLE 18

Preparation of methyl 11-[3-(2-methylbutyryloxymethyl)-4-oxo-2-oxetano]-3,5,7-trimethyl-2,4-undecadienoate A solution of the compound from Example 2 (0.034 g, 0.1 mmol) and 2-methylbutyryl anhydride (0.055 g, 0.3 mmol) in anhydrous pyridine (0.25 ml) at ambient temperature under nitrogen for 20 hours. The reaction mixture was diluted with methylene chloride evaporated in vacuo and then washed with toluene several times to provide a colorless viscous gum. The crude product was purified by preparative thin layer chromatography over silica gel eluted with ethyl acetate:hexane (30:70) to afford the desired product.

EXAMPLE 19

Preparation of methyl 11-[3-(N-methylurethanylmethyl)-4-oxo-2-oxetano]-3,5,7-trimethyl-2,4-undecadienoate To a solution of the compound of Example 2 (37 mg, 0.11 mmol) in pyridine (0.5 ml) was added methyl isocyanate (1 ml) and the reaction mixture heated at about 55° C. for about 16 hours. The excess methyl isocyanate was removed and the residue was purified by preparative thin layer chromatography on silica gel eluted with ethyl acetate:hexane (30:70) to afford the desired product.

NMR($CDCl_3$) δ: 2.81 ppm (d, 3 H) 4.74 ppm (broad s, H) 4.30–4.50 (m, 3 H).

EXAMPLE 20

Preparation of tert-butyl 11-(3-hydroxymethyl-4-oxo-2-oxetano)-3,5,7-trimethyl-2,4-undecadienoate Three portions of O-t-butyl-N,N'-diisopropylisourea (200 mg) were added at 3 hour intervals to a solution of the compound from Example 1 (310 mg, 0.96 mmol) in methylene chloride (2.5 ml) at room temperature. After stirring for an additional 16 hours, the solids were filtered and washed twice with methylene chloride. The residue after evaporation in vacuo was purified by preparative thin layer chromatography to afford the desired product.

NMR ($CDCl_3$) δ 1.50 (S,9H), 3.41 (d of t, 1H), 3.8–4.1 (m, 2H), 4.58 (m, 1H) IR 1820 $cm^{-1}$, 1730 $cm^{-1}$.

EXAMPLE 21

Preparation of 11-(3-Chloromethyl-4-oxo-2-oxetano)-3,5,7-trimethyl-2,4-undecadienoic acid (a) tert-Butyl 11-(3-hydroxymethyl-4-oxo-2oxetano-3,5,7-trimethyl-2,4-undecanoate ($2^1a$)

Three portions of O-t-butyl-N,N'-diisopropylisourea (200 mg) were added at 3 hour intervals to a solution of the compound from 11-(3-hydroxymethyl-4-oxo-2-oxetano)-3,5,7-trimethyl-2,4-undecadienoic acid (310 mg, 0.96 mmol) in methylene chloride (2.5 ml) at room temperature. After stirring for an additional 16 hours, the solids were filtered and washed twice with methylene chloride. The residue after evaporation in vacuo was purified by preparative thin layer chromatography to afford the desired product.

NMR ($CDCl_3$) δ 1.50 (s,9H), 3.41 (d of t, 1H), 3.8–4.1 (m, 2H) 4.58 (m, 1H) IR 1820 $cm^{-1}$, 1703 $cm^{-1}$.

(b) tert-Butyl 11-(3-chloromethyl-4-oxo-2-oxetano)-3,5,7-trimethyl-2,4-undecanoate (21b)

A mixture of the compound (21a) (18 mg) and polymer supported triphenylphosphine (40 mg) in carbon tetrachloride (0.5 ml) was stirred and heated under reflux in a nitrogen atmosphere for 1 hour. The resin was filtered and washed with ethyl acetate (3x). Evaporation in vacuo and TLC purification (silica gel, 7% MeOH-$CH_2Cl_2$ gave the desired product. NMR δ 1.51 (s, 9H, OC($CH_3$)$_3$), 3.61 (m, 1H, 13-H), 3.82 (m, 2H, $CH_2Cl$), 4.51 1H, 12-H).

(c) 11-(3-Chloromethyl-4-oxo-2-oxetano)-3,5,7-trimethyl-2,4-undecadienoic acid

A solution of the compound (21b) (7 mg) in 10% trifluroacetic acid—$CH_2Cl_2$ (300 μl) was kept at room temperature for 1.5 hours. After cooling in an ice bath nd dilution with 1 ml each of ice cold $CH_2Cl_2$ and $H_2O$, the aqueous phase was extracted with $CH_2Cl_2$ (2x), an the combined organic extracts were washed with $H_2O$ and dried ($MgSO_4$). Evaporation in vacuo and purification by TLC (silica gel, 7% MeOH-$CH_2Cl_2$) gave the desired product. NMR δ 3.62 (m, 1H, 13-H), 3.81 (m, 2H, $CH_2Cl_2$), 4.51 (m, 1H, 12-H).

EXAMPLE 22

Preparation of 11-(3-bromomethyl-4-oxo-2-oxetano)-3,5,7 trimethyl-2,4-undecadienoic acid A solution of triphenylphosphine ($Ph_3P$) (31 mg, 0.118 mmoles) in THF (0.2 ml) was added dropwise with vigorous stirring at room temperature to a solution of N-bromosuccinamide (NBS) (21 mg, 0.118 mmoles). To the suspension was added a solution of the compound (21a) (43 mg, 0.117 mmoles) in THF (0.2 ml). After stirring at room temperature for 1 hour, NBS (4 mg) and $Ph_3P$ (6 mg) were added. After stirring for 2 hours more, the solid was filtered and washed with THF (3x). The filtrate was purified by TLC (hexane EtOAc 9:1, silica gel) to give the tert-butyl ester of the desired product. NMR δ 1.50 (s, 9H, OC(CH$_3$)$_3$), 3.65 (m, 3H, CH$_2$Br+13-H) 4.46 (m, 1H, 13-H).

Removal of the tert-butyl group was accomplished by the same procedure of Example (21c) and gave the desired product. NMR δ 3.63 (m, 3H, CH$_2$Br+13-H), 4.44 (m, 1H, 12-H).

EXAMPLE 23

Preparation of 11-(3-fluoromethyl-4-oxo-2-oxetano)-3,5,7,-trimethyl-2,4-undecadienoic acid To a solution of diethylaminosulfur trifluoride (25 µl, 0.20 mmole) in CH$_2$Cl$_2$ (125 ml) cooled to −78° was added dropwise over 5 minutes with magnetic stirring in a N$_2$ atmosphere a solution of the compound (21a) (57 mg, 0.15 mmole) in CH$_2$Cl$_2$ (125 µl). After 5 minutes the mixture was allowed to warm to room temperature (approx. 15 minutes), cooled to 0° and quenched with 0.5 ml of saturated NaHCO$_3$ solution. After dilution with CH$_2$Cl$_2$ and H$_2$O, the aqueous phase was extracted with CH$_2$Cl$_2$ (3x). The combined CH$_2$Cl$_2$ phases were washed with H$_2$O and dried (MgSO$_4$). Purification of TLC (silica gel hexane EtOAc 4:1) gave the tert-butyl ester of the desired product. NMR δ 1.50 (S, 9H, OC(CH$_3$)$_3$), 3.54 (m, 1H, 13-H), 4.5–5.0 (m, 3H, CH$_2$F+12-H).

Removal of the tert-butyl group was accomplished by the same procedure of Examples (21c) and gave the desired product. NMR δ 3.54 (m, 1H, 13-H), 4.5–5.0 (m, 3H, CH$_2$F+12-H).

EXAMPLE 24

Preparation of 11-(3-methyl-4-oxo-2-oxetano)-3,5,7-trimethyl-2,4-undecadienoic acid A solution of the compound of Example (21a) (25 mg, 0.058 mmoles) and nBu$_3$SnH (24 µl, 0.087 mmoles) in toluene (250 ml) was warmed at 55° for 4 hours in a N$_2$ atmosphere. The cooled reaction mixture was purified by TLC (silica gel, hexane-EtOAc 9:1) to give the tert-butyl ester of the desired compound. NMR δ 1.49 (s, 9H, OC(CH$_3$)$_3$), 1.39 (d, 3H, 13-CH$_3$), 3.23 (dxq, 1H, 13-H), 4.16 (m, 1H, 12-H).

Removal of the tert-butyl was accomplished by the same procedure of Example (21c) and gave the desired product. NMR δ 1.39 (d, 3H, 13-CH$_3$), 3.23 (dxq, 1H, 13-H), 4.18 (m, 1H, 12-H).

EXAMPLE 25

Preparation of methyl 11-(3-cyanomethyl-4-oxo-2-oxetano)-3,5,7-trimethyl-2,4-undecadienoate (a) Methyl 11-(3-methanesulfonyloxy-methyl-4-oxo-2-oxetano)-3,5,7-trimethyl-2,4-undecadienoate (25a)

To a solution of methyl 11-(3-hydroxymethyl-4-oxo-2-oxetano)-3,5,7 trimethyl-2,4-undecadienoate (100 mg) and triethylamine (150 mg) in methylene chloride (5 ml) at 0° C. to 5° C. was added a solution of methanesulfonyl chloride (150 mg) in methylene chloride (0 5 ml) during 10 minutes. The mixture was stirred at 0° to 5° for ½ hour and then at room temperature for ½ hour. The desired product was isolated via preparative TLC purification. 200 MHz NMR δ 3.08 ppm (s, 3H, CH$_3$SO$_3$—).

(b) Methyl 11-(3-cyanomethyl-4-oxo-2-oxetano-3,5,7-trimethyl-2,4-undecadienoate (25b)

To a solution of the compound (25a) (10 mg) in dimethyl sulfoxide (0.5 ml) and dimethoxymethane (0.5 ml) at 5° C. was added a solution of sodium cyanide (0.9 mg) in dimethyl sulfoxide (0.3 ml) during 10 minutes. The mixture was stirred at 5° for 17 hours. Purification of the reaction mixture via preparative TLC gave the desired product.

EXAMPLE 26

Preparation of methyl 11-(3-acetylthiomethyl-4-oxo-2-oxetano)-3,5,7-trimethyl-2,4-undecadienoate Diisopropyl azodicarboxylate (0.052 ml, 0.266 mmole) was added to a stirred solution of triphenylphosphine (0.07 g, 0.266 mmole) in dry THF (0.5 ml) at reflux under nitrogen. The mixture was stirred for 2 hours. To the stirred mixture was then added to a solution of methyl 11-(3-hydroxymethyl-4-oxo-2-oxetano)-3,5,7-trimethyl-2,4-undecadienoate (0.045g, 0.133 mmole) and thiolacetic acid (0.02 ml, 0.266 mmole) in THF (1 ml). After 1 hour at reflux and 2 hours at ambient temperature, the mixture was purified via preparative thin layer chromatography (tlc) on silica gel eluted with EtOAc:hexane (20:80) to afford the desired product.

EXAMPLE 27

Preparation of methyl 11-(3-azidomethyl-4-oxo-2-oxetano)-3,5,7-trimethyl-2,4-undecadienoate Diphenylphosphine azide (0.043 ml, 0.2 mmole) was added to a stirred solution of methyl 11-(3-hydroxyethyl-4-oxo-2-oxetano)-3,5,7-trimethyl-2,4-undecadienoate (0.034g, 0.1 mmole) and triphenyl-phosphine (0.053g, 0.2 mmoles) in dry THF (0.6 ml) at reflux under nitrogen. Diisopropylazodicarboxylate (0.04 ml) was added to the mixture and after 1 hour at reflux and 1 hour at ambient temperature, the mixture was purified via preparative tlc on silica gel eluted with EtOAc:hexane (15:85) to afford the desired product.

EXAMPLE 28

Preparation of methyl 11-(3-methylene-4-oxo-2-oxetano)-3,5,7-trimethyl-2,4-undecadienoate Utilizing the procedure of Example 25, Step (a) the above titled compound was also prepared and isolated as a minor component.

NMR δ 5.42

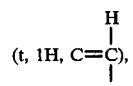

5.9.3

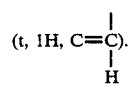

EXAMPLE 29

Preparation of Alkali and Alkaline Earth Salts of Compound I wherein $R^1$ is hydroxide To a solution of the lactone from Example 21 (42 mg) in ethanol (2 ml) is added aqueous NaOH (1 equivalent). After one hour at room temperature, the mixture is taken to dryness in vacuo to yield the sodium salt of Compound I, wherein $R^4$ is hydroxy.

In like manner, the potassium salt is prepared using one equivalent of potassium hydroxide, and the calcium salt using one equivalent of CaO.

EXAMPLE 30

As a specific embodiment of an oral composition of a compound of this invention, 20 mg of the lactone from Example 21 is formulated with sufficient finely divided lactose to provide a total amount of 580 to 590 mg to fill a size 0 hard gelatin capsule.

EXAMPLE 31

As a specific embodiment of a parenteral composition of a compound of this invention, 20 mg of the lactone from Example 21, as the sodium salt, is dissolved in sterile water, buffered to a pH of 7 with 1.0 mM potassium phosphate buffer solution to a concentration of 2.0 percent and is placed in a sterile ampule for parenteral administration.

EXAMPLES 32 TO 37

Preparation of E-3-methyl-4-(substituted)-2-oxetanones

1. Ethyl threo-3-hydroxy-2-methyl-12-tridecenoate

To 8.6 ml g 1.0M lithium diisopropylamide (LDA), prepared from 2.20 ml of diisopropylamine, 6.3 ml of 2.5N nBuLi in hexane, and 9.5 ml of THF was added ethyl acetate (0.7325 ml, 7 5 mmoles) dropwise maintaining the temperature $<-45°$ C. After 10 minutes, 10 undecenal (1.09 g, 6.5 mmoles) was added dropwise keeping the temperature $<-30°$ C. The temperature was allowed to rise to $-15°$ C., kept there for 15 minutes, lowered to $-50°$ C. and 9.4 ml of the above LDA solution was added maintaining the temperature $<-30°$ C. After 15 minutes at $-20°$ C., the cooling bath was removed and a solution of MeI (0.70 ml, 11.25 mmoles) in HMPA (1.75 ml) was added rapidly. After 15 minutes at room temperature, the mixture was warmed at 35° C. for 5 minutes and poured into 1M $H_2SO_4$ (45 ml) and $Et_2O$ (25 ml). The aqueous phase was extracted with $Et_2O$ (2x), and the combined $Et_2O$ phases were washed with $H_2O$ (2x) and saturated brine and dried ($MgSO_4$). The crude material after evaporation in vacuo was flashed chromatographed on silica gel with hexane-EtOAc (9:1) to give pure ethyl threo-3-hydroxy-2-methyl-12-tridecenoate.

NMR: ($CDCl_3$) δ 5.80 (m, 1H, CH=CH$_2$), 4.94–5.03 (m, 2H, CH=CH$_2$), 4.16 (q, 2H, OCH$_2$CH$_3$), 3.64 (m, 1H, CHOH), 2.57 (d, 1H, OH), 2.50 (m, 1H, CHCH$_3$), 2.02 (q, 2H, CH$_2$CH=), 1.27 (t, 3H, OCH$_2$CH$_3$), 1.19 (d, 3H, CH$_3$CH).

The following compounds were prepared using essentially the same method:

Ethyl threo-3-hydroxy-2-methyltridecanoate: NMR: δ 4.17 (q, 2H, OCH$_2$CH$_3$), 3.64 (brs, 1H, CHOH), 2.57 (d, 1H, OH), 2.50 (m, 1H, CHCH$_3$), 1.26 (t, 2H, OCH$_2$CH$_3$), 1.21 (d, 3H, CHCH$_3$), 0.88 (t, 3H, 13—CH$_3$).

Ethyl threo-3-hydroxy-2-methyl-7-phenyloctanoate: NMR: δ 7.1–7.4 (m, 5H, ArH), 4.17 (q, 2H, OCH$_2$CH$_3$), 3.64 (brs, 1H, CHOH), 2.61 (t, 2H, CH$_2$Ph), 2.48 (m, 2H, CHCH$_3$), 1.26 (t, 3H, OCH$_2$CH$_3$), 1.20 (d, 3H, CH$_3$CH).

Ethyl threo-3-hydroxy-2-methyl-8-phenylnonanoate: NMR: δ 7.1–7.4 (m, 5H, ArH), 4.17 (q, 2H, OCH$_2$CH$_3$), 3.62 (brs, 1H, CHOH), 2.60 (t, 2H, CH$_2$Ph), 2.50 (m, 2H, CHCH$_3$), 1.27 (t, 3H, OCH$_2$CH$_3$), 1.21 (d, 3H, CHCH$_3$).

Ethyl threo-3-hydroxy-2,5,9,13-tetramethyltetradecanoate: NMR: δ 4.17 (q, 2H, OCH$_2$CH$_3$), 3.75 (brs, 1H, CHOH), 2.54 (d, 1H, OH), 2.49 (m, 1H, CHCH$_3$).

2. E-3-Methyl-4-(6-phenylhexyl)-2-oxetanone

A mixture of ethyl threo-3-hydroxy-2-methyl-8-phenylnonanoate (110 mg) and 1 ml of 1.7M KOH in ethanol-$H_2O$ (1:1) was stirred at room temperature in a $N_2$ atmosphere for 3 hours. The clear solution was diluted with $H_2O$. extracted with $Et_2O$, acidified with concentrated HCl, and extracted with $Et_2O$ (3x). The combined $Et_2O$ extracts were washed with $H_2O$ and saturated brine and dried (MgSO$_4$). Evaporation in vacuo gave threo-3-hydroxy-2-methyl-8-phenyl-nonanoic acid.

A solution of threo-3-hydroxy-2-methyl-8-phenyl-nonanoic acid (88 mg, 0.33 mmole) in pyridine (2 ml) was cooled to $-15°$ C. and p-toluenesulfonyl chloride (127 mg, 0.66 mmole) was added. After stirring several minutes, the solution was kept at 3° C. for 20 hours. The red brown solution was poured onto ice cold 1M $H_2SO_4$-$Et_2O$. The aqueous phase was extracted with $Et_2O$ (2x). The combined $Et_2O$ phases were washed with $H_2O$ saturated NaHCO$_3$ solution, saturated brine, and dried (MgSO$_4$). The residue after evaporation in vacuo was purified by TLC (silica gel, hexane-EtOAc 9:1) to give E-3-methyl-4-(6-phenylhexyl)-2-oxtanone. IR 1822 cm$^{-1}$ (C=O); NMR: δ 7.1–7.4 (m, 5H, ArH), 4.16 (dxt, 1H, 4-H), 3.22 (dxg, 1H, 3-H, J 3,4=4.0 Hz), 2.60 (t, 2H, CH$_2$Ph), 1.38 (d, 3H, CHCH$_3$).

The following compounds were prepared using essentially the same method:

Compound No.

33 E-3-Methyl-4-decyl-2-oxetanone: NMR: δ 4.18 (dxt, 1H, 4-H), 3.23 (dxg, 1H, 3-H, J 3,4,=4.0 Hz), 1.41 (d, 3H, CHCH$_3$), 0.88 (t, 3H, CH$_3$CH$_2$).

34 E-3-Methyl-4-(5-phenylpentyl)-2-oxetanone: IR 1825 cm$^{-1}$ (C=O); NMR: δ 7.1–7.35 (m, 5H, ArH), 4.15 (dxt, 1H, 4-H), 3.20 (dxg, 1H, 3-H, J 3,4=4.0 Hz), 2.61 (t, 2H, CH$_2$Ph), 1.37 (d, 3H, CHCH$_3$).

35 E-3-Methyl-4-(9-decenyl)-2-oxetanone: NMR: δ 5.81 (m, 1H, CH=CH$_2$), 4.9–5.1 (m, 2H, CH=CH$_2$), 4.16 (dxt, 1H, 4-H), 3.20 (dxq, 1H, 3-H, J 3,4=3.9 Hz), 2.03 (g, 2H, CH$_2$CH=), 1.37 (d, 3H, CH$_3$CH).

36 E-3-Methyl-4-(9-decynyl)-2-oxetanone: IR 1825 cm$^{-1}$ (C=O), 2110cm$^{-1}$ (C=C). NMR: δ 4.17 (dxt, 1H, 4-H), 3.22 (dxq, 1H, J 3,4=4.0 Hz, 3-H), 2.19 (m, 2H, CH$_2$C=C), 1.94 (t, 1H, C≡CH), 1.38 (d, 3H, CHCH$_3$).

37 E-3-Methyl-4-(9-oxodecyl)-2-oxetanone: NMR: δ 4.18 (dxt, 1H, 4-H), 3.21 (dxq, 1H, J 3,4=4.0, 3-H), 2.42 (t, 2H, 2.12 (S, 3H 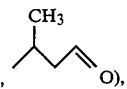

1.38 (d, 3H, CH₃CH).

EXAMPLE 38

Preparation of E-3-Methyl-4-(9-oxodecyl)-2-oxetanone

1. Threo-3-hydroxy-2-methyl-12-tridecynoic acid

To a solution of threo-3-hydroxy-2-methyl-12-tridecenoic acid (420 mg, 1.74 mmoles) in CH₂Cl₂ (2 ml) cooled to 0° C. was added dropwise Br₂ (94 ml, 1.81 mmoles). The mixture was kept at room temperature for 10 minutes, and the solvent removed in vacuo to give the 12,13 dibromo compound.

A solution of the above dibromo compound in 3 ml of Et₂O was added to a suspension of NaNH₂ (prepared from 220 mg of Na) in 15 ml of liquid NH₃. After stirring for 4 hours in a N₂ atmosphere, the NH₃ was allowed to evaporate overnight. The residue was dissolved in concentrated NH₄OH (20 ml) and filtered. The filtrate was washed with Et₂O, acidified with concentrated HCl and extracted with Et₂O (3x). The combined Et₂O extracts were washed with H₂O and saturated brine and dried (MgSO₄). Evaporation in vacuo gave threo-3-hydroxy-2-methyl-12-tridecynoic acid.

NMR: δ 3.70 (brs, 1H, CHOH), 2.56 (m, 1H, CHCH₃), 1.94 (t 1H, C≡CH), 1.24 (d, 3H, CHCH₃).

2. Threo-3-hydroxy 2-methyl-12-oxotridecanoic acid

A solution of threo-3-hydroxy-2-methyl-12-tridecynoic acid (160 mg, 0.67 mmoles) in 1 ml of 90% EtOH was stirred with 50 mg of Hg/Nafion-H [*Synthesis*, 671 (1978)] at room temperature for 8 hours and then at 43° C. for 30 minutes. The resin was filtered and washed EtOH (2x) and Et₂O (3x). The filtrate and washes were diluted with H₂O and extracted with Et₂O (3x). The combined Et₂O extracts were washed with H₂O and saturated brine and dried (MgSO₄). Evaporation in vacuo gave threo-3-hydroxy-2-methyl-12-oxo-tridecanoic acid.

NMR: δ 3.48 (brs, 1H, CHOH), 2.57 (m, 1H, CHCH₃), 2.42 (t, 2H, CH₂CO), 2.12 (s, 3H, COCH₃), 1.25 (d, 3H, CHCH₃).

3. E-3-Methyl-4-(9-oxodecyl)-2-oxetanone

Utilizing the general procedure of Example 32, Step 2, the above noted compound was obtained from threo-3-hydroxy-2-methyl-12-oxo-tridecanoic acid.

NMR: δ 4.18 (dxt, 1H, 4-H), 3.21 (dxq, 1H, J=4.0 H₂=Hz), 2.42 (t, 2H, CH₂CO), 2.12 (5, 3H, CH₃CO), 1.38 (d, 3H, CH₃CH).

EXAMPLE 39

Preparation of 8-(3-methoxymethyl-4-oxo-2-oxetanyl)-4-methyl-2-octanone

To a solution of 400 mg (1.135 mmole) of methyl 11-(3-methoxymethyl-4-oxo-2-oxetanyl)-3,5,7-trimethyl-2,4-undecadienoate in 10 ml of CHCl₂ at −78° C., was bubbled ozone for 8 minutes. The resulting mixture was stirred for 30 minutes at −78° C. then at room temperature for another 30 minutes. Acetic acid and zinc dust were added. After stirring for 1 hour at room temperature, the solution was filtered and the filtrate was concentrated to dryness. The product was purified by flash column chromatography to give 8-(3-methoxymethyl-4-oxo-2-oxetanyl)-4-methyl-2-octanone as a colorless oil.

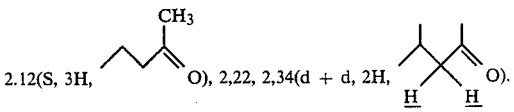

EXAMPLE 40

Preparation of 8-(3-methoxymethyl-4-oxo-2-oxetanyl)-4-methyl-2-octanol 40 mg (0.156 mmole) of 8-(3-methoxymethyl-4-oxo-2-oxetanyl)-4-methyl-2-octanone in 5 ml of MeOH, was added 10 mg of sodium borohydride. The mixture was stirred for 5 minutes at room temperature. The product was purified by flash column chromatography (30% EtOAc in hexane) to afford 8-(3-methoxymethyl-4-oxo-2-oxetanyl-4 methyl-2-oxetanol as an oil.

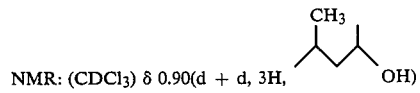

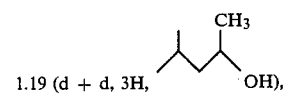

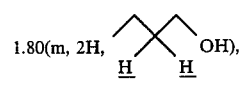

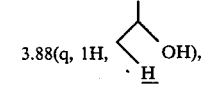

EXAMPLE 41

Preparation of 8-(3-methoxymethyl-4-oxo-2-oxetanyl)-4methyl-2-methoxyoctane 10 mg of 8-(3-methoxymethyl-4-oxo-2-oxetanyl)-4-methyl-2-octanol in 1 ml of EtOAc was added a small amount of activated silver oxide and 0.5 ml of methyl iodide. The mixture was heated for 5.5 hours at 60° C. The solution was filtered and the filtrate was concentrated to dryness. The product was purified by flash chromatography to yield 8-(3-methoxymethyl-4-oxo-2-oxetanyl)-4-methyl-2-methoxyoctane.

NMR: (CDCl₃) = δ 0.87(d + d, 3H, 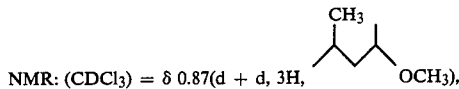

1.11(d + d, 3H, 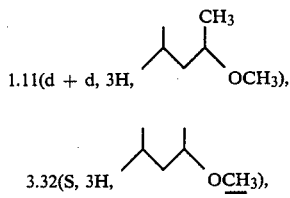

3.32(S, 3H, O<u>CH</u>₃),

EXAMPLE 42

Preparation of 11-(3-hydroxymethyl-4-oxo-2-oxetanyl)-4,5-oxiranyl-4,5,7-trimethyl-2-undecenoic acid 65 mg (0.20 mmole) of 11-(3-hydroxymethyl-4-oxo-2-oxetanyl)-3,5,7-trimethyl-2,4-undecadienoic acid in 3 ml of CH₂Cl₂ was added 0.12 mg (0.7 mmole) of m-chloroperoxybenzoic acid. The resulting mixture was stirred for 2 hours at room temperature. The product was purified by prep. TLC (5% MeOH in CH₂Cl₂) to yield 11-(3-hydroxymethyl-4-oxo-2-oxetanyl)-4,5-oxiranyl-3,5,7-trimethyl-2-undecenoic acid.

NMR: (CDCl₃) = δ 1.14(S, 3H, 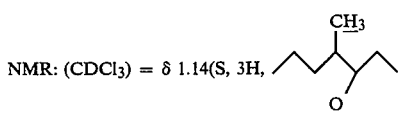

EXAMPLE 43

Preparation of Methyl-11-(3-hydroxymethyl-4-oxo-2-oxetanyl)-4,5-oxiranyl-3,5,7-trimethyl-2-undecenoate Similarly, following the procedure of Example 42, but substituting methyl 11-(3-hydroxymethyl-4-oxo-2-oxetanyl)-3,5,7 trimethyl-2,4-undecadienoate for 11-(3-hydroxymethyl-4-oxo-2-oxetanyl)-3,5,7-trimethyl-2,4-undecadienoic acid yielded methyl 11-(3-(hydroxymethyl)-4-oxo-2-oxetanyl)-4,5-oxiranyl-3,5,7-trimethyl-2-undecenoate.

NMR: (CDCl₃) = δ 1.14(S, 3H, 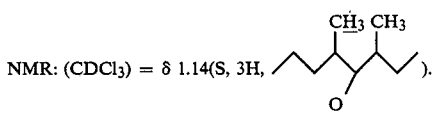

EXAMPLE 44

Preparation of Methyl-11-(3-hydroxymethyl-4-oxo-2-oxetanyl)-4,5-dihydroxy-3,5,7-trimethyl-2-undecenoate To a solution of 20 mg (0.059 mmole) of methyl 11-(3-hydroxymethyl-4-oxo-2-oxetanyl)-3,5,7-trimethyl-2,4-undecadienoate in 3 ml of EtOAc at 0° C. was added 100 ml of pyridine, then added 200 ml of osmium tetroxide-ether solution (1 g/10 ml, 20 mg). The mixture was stirred for 1 hour at 0° C., then 1 hour at room temperature until the solution turned brown. The solution was concentrated to dryness. The residue was redissolved in 10 ml of CH₂Cl₂. The CH₂Cl₂ solution then was added to an aqueous sodium bisulfate solution (1 g in 8 ml of H₂O). The mixture was stirred overnight. The organic layer was separated, dried and concentrated. The product was purified by prep. TLC (hexane:EtOAc=1:1) to give methyl 11-(3-hydroxymethyl-4-oxo-2-oxetanyl)-4,5-dihydroxy-3,5,7-trimethyl-2-undecenoate.

NMR: (CDCl₃) = δ 1.14(S, 3H, 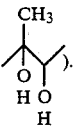

EXAMPLE 45

Preparation of Methyl-11-(3-methoxymethyl-4-oxo-2-oxetanyl)-4,5-dihydroxy-3,5,7-trimethyl-2-undecenoate 10 mg of methyl 11-(3-hydroxymethyl-4-oxo-2-oxetanyl)-4,5 dihydroxy-3,5,7-trimethyl-2-undecenoate in 2 ml of EtOAc was added 35 mg of silver oxide and 0.3 ml of methyl iodide. The mixture was heated at 53° C. overnight. The solution was filtered and concentrated by dryness. The product was purified by prep. TLC (EtOAc:Hexane=1:1) to afford methyl 11-(3-methoxymethyl-4-oxo-2-oxetanyl)-4,5-dihydroxy-3,5,7-trimethyl-2-undecenoate.

NMR: (CDCl₃) δ 1.13(S, 3H, 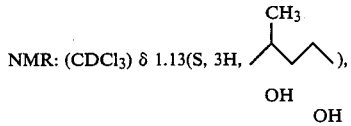

3.40(S, 3H, CH₃O 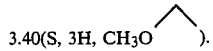 ).

EXAMPLE 46

Preparation of methyl-11-(3-methoxymethyl-4-oxo-2-oxetanyl)-3,5,7-trimethyl-2-undecenoate 1. Methyl 11-(3-hydroxymethyl-4-oxo-2-oxetanyl)-3,5,7-trimethyl-2-undecenaote 49 mg (0.144 mmole) of Methyl 11-(3-hydroxymethyl-4-oxo-2-oxetanyl)-3,5,7-trimethyl-2,4-undecadienoate in 5 ml of EtOAc was added 3 mg of platinium oxide. This mixture was hydrogenated at room temperature and 1 atmosphere for 30 minutes (0.144 mmole (1 eq) of hydrogen was consumed). The solution was filtered and the filtrate was concentrated to dryness afforded methyl 11-(3-hydroxymethyl-4-oxo-2-oxetanyl)-3,5,7-trimethyl-2-undecenoate.

NMR (CDCl₃): δ 0.83(m,6H), 5.62(s,1H).

2. Methyl 11-(3-methoxymethyl-4-oxo-2-oxetanyl)-3,5,7-trimethyl-2-undecenoate

Similarly, following the procedure of Example 46, Step 1, but substituting methyl 11-(3-methoxymethyl-4-oxo-2-oxetanyl)-3,5,7-trimethyl-2,4-undecadienoate for methyl 11-(3-hydroxymethyl-4-oxo-2-oxetanyl)-3,5,7-trimethyl-1,4-undecadienoate, afforded methyl 11-(3-methoxymethyl-4-oxo-2-oxetanyl)-3,5,7-trimethyl-2-undecenoate.

EXAMPLE 47

Preparation of Alkali and Alkaline Earth Salts of Compound I wherein $R^1$ is $COR^4$ and $R^4$ is hydroxy To a solution of the lactone from Example 32 (42 mg) in ethanol (2 ml) is added aqueous NaOH (1 equivalent). After one hour at room temperature, the mixture is taken to dryness in vacuo to yield the sodium salt of Compound I, wherein $R^1$ is carboxy.

In like manner, the potassium salt is prepared using one equivalent of potassium hydroxide, and the calcium salt using one equivalent of CaO.

EXAMPLE 48

As a specific embodiment of an oral composition of a compound of this invention, 20 mg of the lactone from Example 32 is formulated with sufficient finely divided lactose to provide a total amount of 580 to 590 mg to fill a size 0 hard gelatin capsule.

EXAMPLE 49

As a specific embodiment of a parenteral composition of a compound of this invention, 20 mg of the lactone from Example 32, as the sodium salt, is dissolved in sterile water, buffered to a pH of 7 with 1.0 mM potassium phosphate buffer solution to a concentration of 2.0 percent and is placed in a sterile ampule for parenteral administration.

What is claimed is:

1. A method for the treatment of ketoacidosis which comprises administering to a subject in a ketoacidotic state an effective amount of a compound represented by the following structural formula (I):

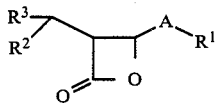

wherein:
$R^1$ is selected from
  (1) hydrogen,
  (2) hydroxy,
  (3) $C_{1-6}$ alkoxy
  (4) phenyl,
  (5) $COR^4$,
$R^4$ is
  (1) hydroxy,
  (2) $C_{1-6}$ alkoxy,
  (3) substituted $C_{1-6}$ alkoxy in which the substituent is a phenyl group,
  (4) amino,
  (5) $C_{1-6}$ alkylamino,
  (6) substituted $C_{1-6}$ alkylamino in which the substituent is a hydroxy group,
  (7) phenylamino,
  (8) substituted phenyl amino in which the substituent is a halogen; and
  (9) 2-thiopyridine;
$R^2$ is selected from
  (1) hydrogen,
  (2) halogen,
  (3) cyano,
  (4) azido,
  (5) $C_{1-6}$ alkylcarbonylthio,
  (6) $C_{1-6}$ alkyl
  (7) $C_{1-6}$ alkoxy,
  (8) $C_{2-6}$ alkenyloxy,
  (9) formyloxy,
  (10) $C_{1-6}$ alkylcarbonyloxy,
  (11) carboxy $C_{1-6}$ alkylcarbonyloxy,
  (12) anisyldiphenylmethyloxy,
  (13) $C_{1-6}$ alkylsulfonyloxy,
  (14) aminocarbonyloxy, and
  (15) $C_{1-6}$ alkylaminocarbonyloxy;
$R^3$ is selected from
  (1) hydrogen,
  (2) $C_{1-6}$ alkyl,
  (3) $C_{1-6}$ alkenyl,
  (4) phenyl, or
$R^2$ and $R^3$ when taken together with the carbon atom to which the are attached form $C_{3-6}$ carbocyclic ring;
A is selected from

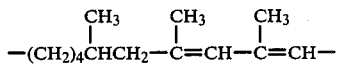

(2) $C_{6-17}$ alkylene,
  (3) substituted $C_{6-17}$ alkylene in which the one or two substituents are
    (a) oxo,
    (b) epoxy,
    (c) geminal dihydroxy,
    (d) $C_{1-6}$ alkoxy, and
    (e) 4-bromophenylhydrazono;
  (4) monounsaturated $C_{6-17}$ alkylene, and
  (5) substituted monounsaturated $C_{6-17}$ alkylene in which the one or two substituents are
    (a) oxo,
    (b) epoxy,
    (c) geminal dihydroxy,
    (d) $C_{1-6}$ alkoxy, and
    (e) 4-bromophenylhydrazono;
  (6) $C_{7-16}$ aralkylene, wherein the alkyl chain is interupted by a 1,2-, 1,3-, or 1,4-phenylene moiety,
  (7) $C_{6-18}$ alkylene, straight or branched chain, interupted by an oxygen, sulfur or sulfoxide moiety,
  (8) a group of the structure

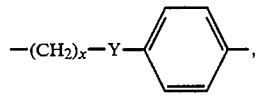

where x is 1–4 and Y is O, S, or SO; the broken line indicates a connecting single or double bond; or a pharmaceutically acceptable salt thereof.

2. The method of claim 1 wherein $R^2$ is hydrogen and the broken line is a connecting single bond.

3. The method of claim 1 wherein $R^2$ is hydrogen and the broken line is a connecting single bond.

4. The method of claim 1 wherein:
$R^4$ is selected from
  (1) amino,
  (2) $C_{1-6}$ alkylamino,
  (3) substituted $C_{1-6}$ alkylamino,
  (4) phenylamino and
  (5) substituted phenylamino.

5. The method of claim 4 wherein $R^2$ is hydrogen.

6. The method of claim 1 wherein A is $C_{6-17}$ alkylene.

7. The method of claim 1 wherein the compound is administered at a daily dosage rate of from about 20 to 2000 mg.

8. The method of claim 7 wherein the compound is administered at a daily dosage rate of from 20 to 100 mg.

9. The method of claim 8 wherein the ketoacidotic subject is a diabetic ketoacidotic subject.

* * * * *